US00PP27092P3

(12) United States Plant Patent
Alcock

(10) Patent No.: US PP27,092 P3
(45) Date of Patent: Aug. 23, 2016

(54) ***ERYNGIUM* PLANT NAMED 'NEPTUNES GOLD'**

(50) Latin Name: *Eryngium zabelii*
Varietal Denomination: NEPTUNES GOLD

(71) Applicant: Neil Alcock, Caernarfon (GB)

(72) Inventor: Neil Alcock, Caernarfon (GB)

( * ) Notice: Subject to any disclaimer, the term of this patent is extended or adjusted under 35 U.S.C. 154(b) by 154 days.

(21) Appl. No.: 14/120,342

(22) Filed: May 14, 2014

(65) Prior Publication Data

US 2015/0334903 P1 Nov. 19, 2015

(51) Int. Cl.
*A01H 5/02* (2006.01)

(52) U.S. Cl.
USPC ..... Plt./361

(58) Field of Classification Search
USPC ..... Plt./361
See application file for complete search history.

*Primary Examiner* — Keith Robinson
(74) *Attorney, Agent, or Firm* — Cassandra Bright

(57) ABSTRACT

A new and distinct *Eryngium* cultivar named 'NEPTUNES GOLD' is disclosed, characterized by golden foliage and large inflorescences. The new cultivar is a *Eryngium*, suitable for ornamental garden purposes.

3 Drawing Sheets

Latin name of the genus and species: *Eryngium zabelii.*
Variety denomination: 'NEPTUNES GOLD'.

BACKGROUND OF THE INVENTION

The new cultivar is a product of chance discovery by the inventor. This new variety, hereinafter referred to as 'NEPTUNES GOLD', was discovered as a chance seedling by the inventor, Neil Alcock. The seed parent is believed to be *Erygium zabelii*, unpatented and the pollen parent undetermined. This interesting new variety was discovered in the inventor's garden during 2008 as an individual seedling plant.

After identifying the new variety as a potentially interesting selection, the inventor first propagated 'NEPTUNES GOLD' by root cuttings during 2009. The inventor continued controlled testing and propagation, assessing stability of the unique characteristics of this variety. Subsequently, several generations have been reproduced and have shown that the unique features of this cultivar are stable and reproduced true to type.

SUMMARY OF THE INVENTION

The cultivar 'NEPTUNES GOLD' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'NEPTUNES GOLD' These characteristics in combination distinguish 'NEPTUNES GOLD' as a new and distinct *Eryngium* cultivar:

1. Unique golden foliage
2. Large flower size

COMPARISON TO PARENT VARIETY

'NEPTUNES GOLD' is similar in most horticultural characteristics to the presumed seed parent variety *Eryngium*

*zabelii*. Plants of the new cultivar 'NEPTUNES GOLD' however, produce unique golden foliage, whereas the seed parent produces green foliage.

COMMERCIAL COMPARISON

'NEPTUNES GOLD' can be compared to the commercial variety *Eryngium zabelii* 'Big Blue' U.S. Plant Pat. No. 20,636. Plants of the new cultivar 'NEPTUNES GOLD' are similar to plants of 'Big Blue' in most horticultural characteristics. Plants of the new cultivar 'NEPTUNES GOLD' however, produce unique golden foliage, which changes color during the seasons, whereas 'Big Blue' has green foliage.

BRIEF DESCRIPTION OF THE PHOTOGRAPHS

The accompanying photograph in FIG. 1 illustrates in full color a typical plant of 'NEPTUNES GOLD' grown outdoors in High Hurstwood, Uckfield, United Kingdom. The plant is approximately 4 years old, and is shown in a 28 cm container.

Figure 1:
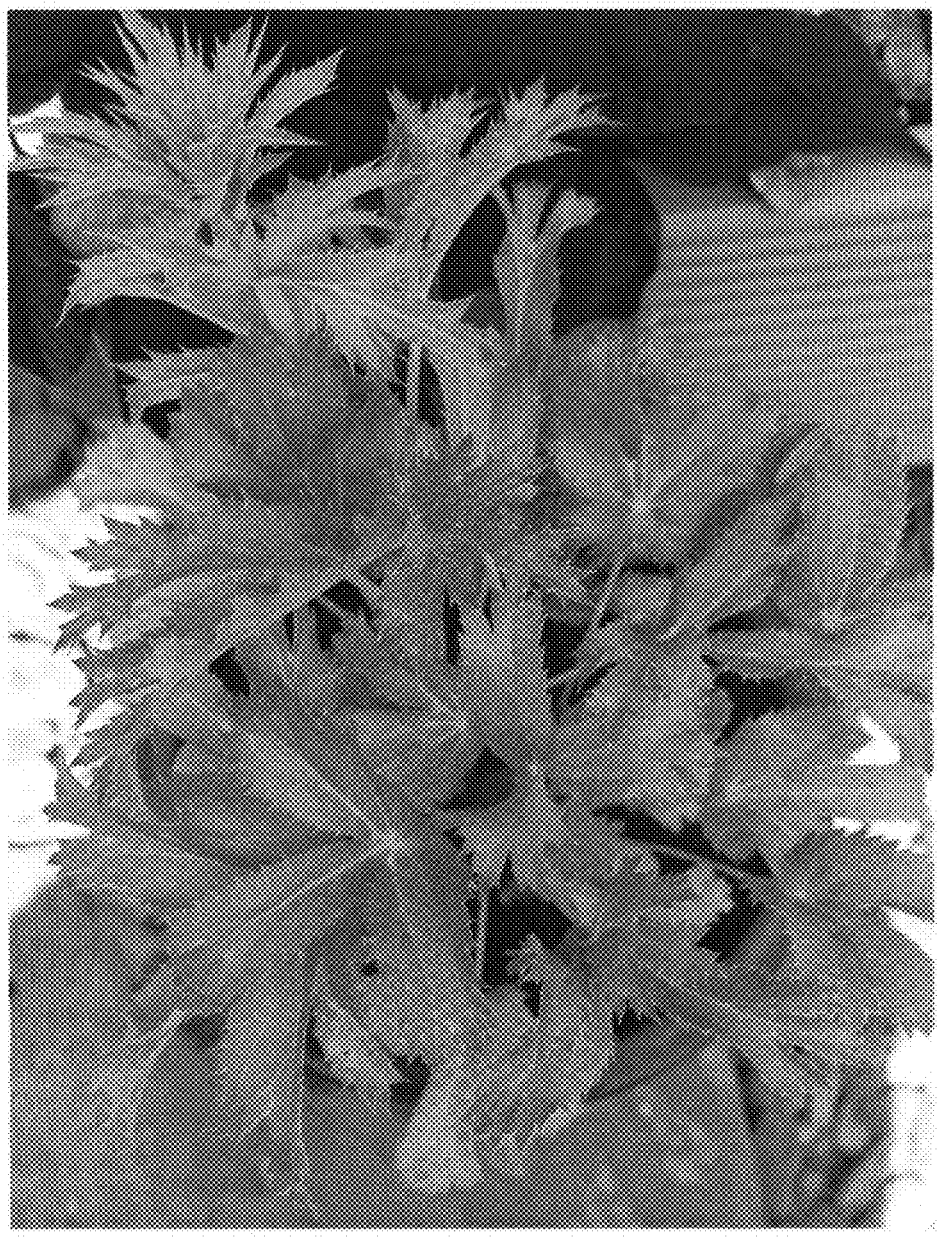
Figure 2:
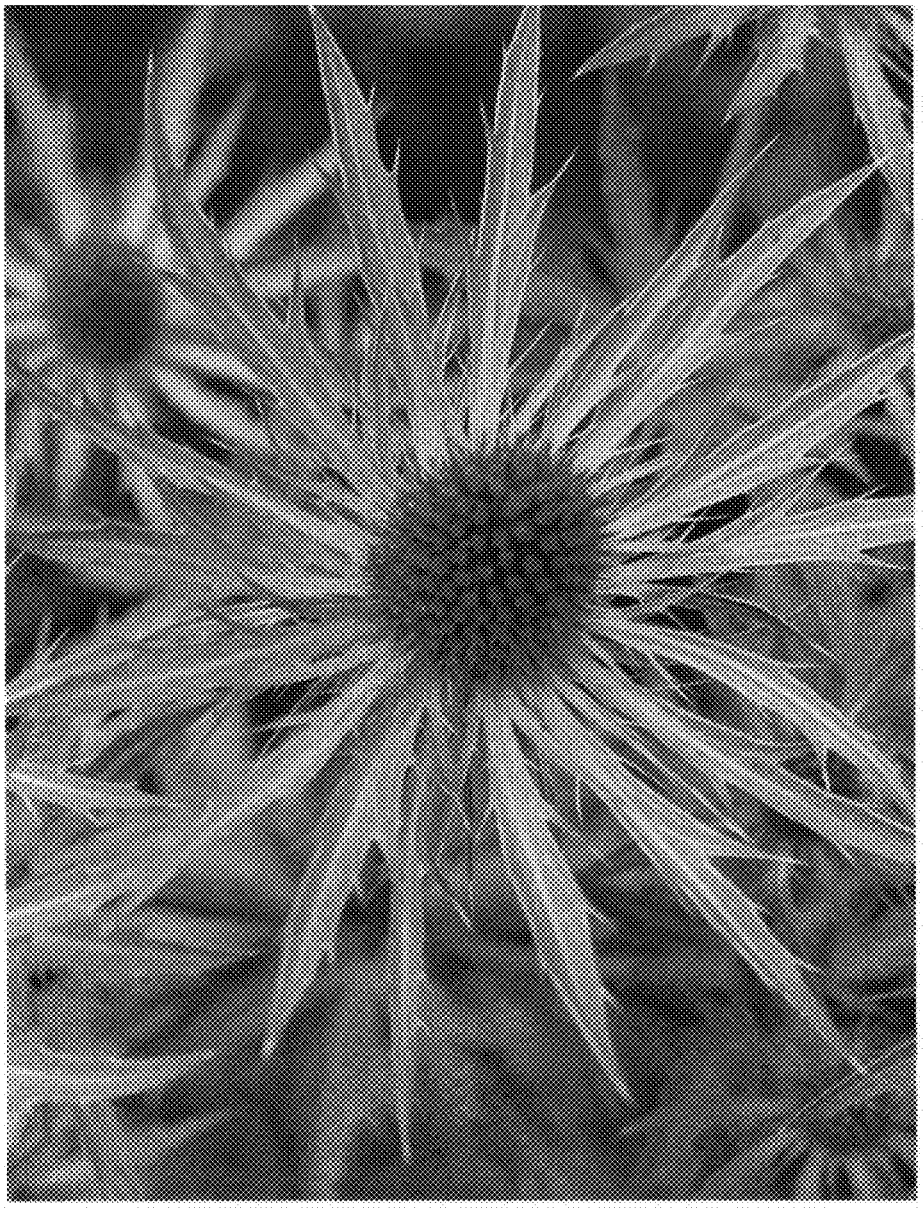
FIG. 2 shows a close up of a typical flower of the new variety.
Figure 3:
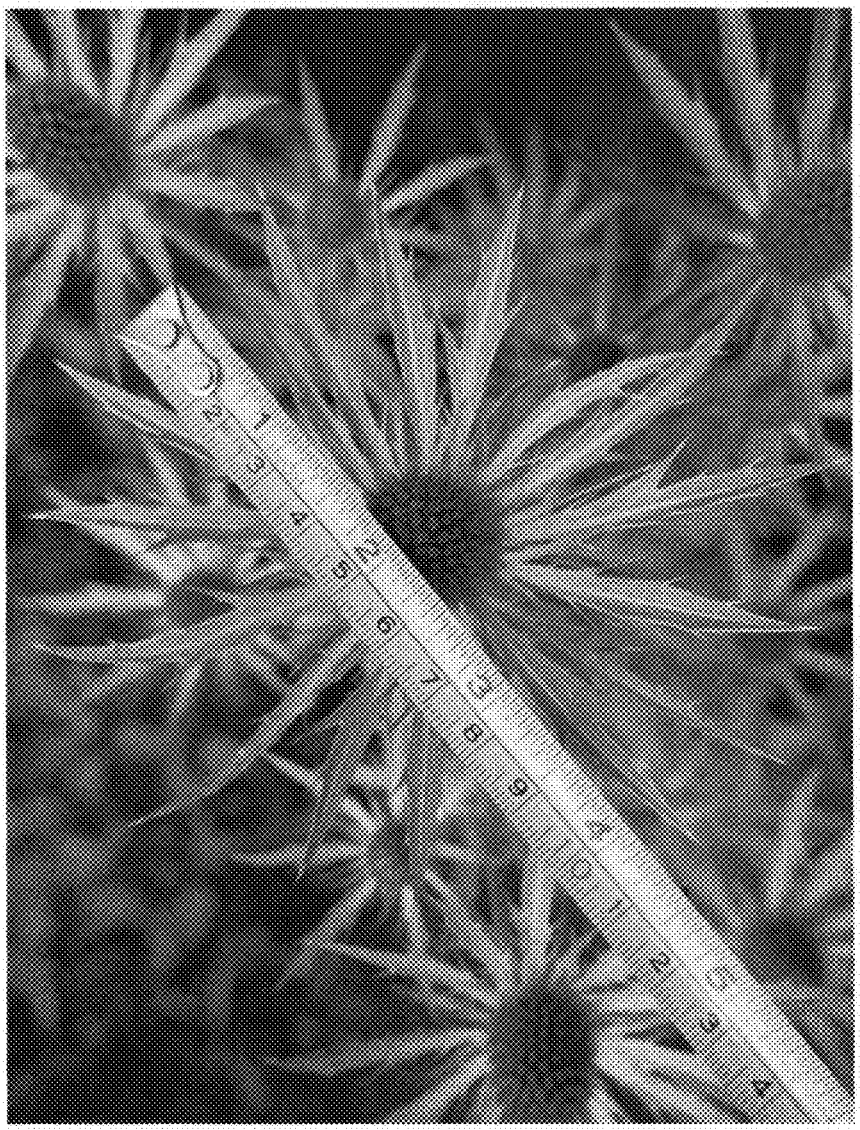
FIG. 3 illustrates a typical flower, with measurement perspective.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'NEPTUNES GOLD' plants grown outdoors in High Hurstwood, Uckfield, United Kingdom. Plants are approximately 4 years old, in a 28 cm nursery container. Measurements and numerical values represent averages of typical plant types.

Botanical classification: *Eryngium zabelii* 'NEPTUNES GOLD'.

PROPAGATION

Time to initiate roots: About 1 month at approximately 20° to 25° C.
Root description: Fine, densely fibrous.
Time to produce a rooted cutting: About 2 months at approximately 20° to 25° C.
Typical propagation method: Root cuttings or tissue culture.
Root description: Fine, fibrous young roots, very well branched.

PLANT

Growth habit: Herbaceous perennial, upright growth habit.
Age of plant described: 4 years.
Container size: 28 cm.
Height: 58 cm.
Plant spread: 40 cm.
Branching characteristics: Flowering stem typically produces 3 to 5 branches.
Primary lateral branches:
*Quantity.*—3 to 5.
*Length.*—8 cm.
*Diameter.*—Approximately 1 cm.
*Quantity.*—3 to 5.
*Texture.*—Smooth, glabrous.
*Color.*—Longitudinal stripes, near RHS 154C and 144B.

FOLIAGE

Leaf:
*Arrangement.*—Alternate, simple.
*Quantity.*—Approximately between 5 and 8 per main branch.
*Average length.*—Approximately 9.5 cm.
*Average width.*—Approximately 10.5 cm.
*Shape.*—Palmately lobed.
*Apex.*—Acuminate.
*Base.*—Cordate.
*Margin.*—Biserrate to serulate, erose, undulate. Prickles at margin, about 1.5 mm to 2.5 mm in length, close to 154D in color.
*Texture of top surface.*—Smooth, glabrous, leathery.
*Texture of bottom surface.*—Smooth, glabrous, leathery.
*Leaf internode length.*—7.5 cm.
*Color.*—Young foliage upper side: Near R.H.S. Yellow-Green 154A flushed with Yellow 6A. Young foliage under side: Near R.H.S. Yellow-Green 154A flushed with Yellow 6A. Mature foliage upper side: Near R.H.S. between Yellow-Green 144B and N144A. Mature foliage under side: Near R.H.S. Yellow-Green 145B.
*Venation.*—Type: Palmatifid. Venation color upper side: Near R.H.S. between 150C and 150D. Venation color under side: Near R.H.S. 145C.
*Petiole.*—Length: 13.7 cm. Width: 4 mm. Color: longitudinal stripes, 154C and 144B. Texture: Smooth, glabrous.

FLOWER

Natural flowering season: May to July (southern UK).
Begins flowering after how many months: 7 months from planting.
Inflorescence type and habit: Single rotate flowers arranged on dense cylindrical flower heads; flowers sessile; inflorescences terminal or arising from leaf axils; freely flowering habit with usually about 145 flowers developing per inflorescence. Flowers face upright and outwardly.
Inflorescence longevity on plant: 25 days, after fully opened. Flowers persistent.
Inflorescence size:
*Diameter.*—Approximately 2.1 cm (excluding involucral bracts), 11.5 cm (including involucral bracts).
*Height.*—Approximately 2.8 cm.
Peduncle:
*Length.*—12 cm.
*Diameter.*—0.7 cm.
*Angle.*—Emerging directly straight up from branch, or at approximately 15° angle from branch.
*Strength.*—Moderately strong and flexible.
*Texture.*—Glabrous.
*Color.*—Near R.H.S. Yellow-Green 144C, occasionally flushed Greyed-Purple N187B.
Individual flower size:
*Diameter.*—Approximately 1.5 cm.
*Height.*—Approximately 1.2 cm.
Petals:
*Petal arrangement.*—Five in a single whorl.
*Size.*—Length: 0.25 cm. Width: 0.15 cm.
*Shape.*—Oblong.
*Margin.*—Entire.
*Apex.*—Emarginate.
*Base.*—Truncate.
*Petal quantity.*—Five.
*Texture.*—Smooth, glabrous, upper and lower surfaces.
Color:
*Petals: When opening.*—Upper surface: A color between R.H.S. between Violet-Blue 95B and Blue 99B, coming 95D towards apex. Lower surface: A color between R.H.S. between Violet-Blue 95B and Blue 99B, coming 95D towards apex.
*Fully opened.*—Upper surface: A color between R.H.S. between Violet-Blue 95B and Blue 99B, coming 95D towards apex. Lower surface: A color between R.H.S. between Violet-Blue 95B and Blue 99B, coming 95D towards apex.
Flower bud:
*Shape.*—Obovate.
*Length.*—Approximately 0.2 cm.
*Diameter.*—Approximately 0.15 cm.
*Color.*—A color between Yellow-Green 150D and 154D, becoming between Blue 101C and 101D at the time of opening.
Sepals:
*Length.*—0.2 cm.
*Width.*—0.1 cm.
*Shape.*—Lanceolate.
*Margin.*—Entire.
*Color.*—Interior Surface: Near R.H.S. Green 137C. Exterior Surface: Near R.H.S. Green 137C.
*Texture.*—Glabrous, upper and lower surfaces.

*Arrangement*.—Rotate.
*Apex*.—Acuminate.
*Base*.—Fused.
Fragrance: None observed.

REPRODUCTIVE ORGANS

Stamens:
*Number*.—5.
*Filament length*.—Approximately 2 mm.
*Filament color*.—Too minute to accurately measure with R.H.S. chart.
Anthers:
*Length*.—Less than 1 mm.
*Shape*.—Linear.
*Color*.—Too minute to accurately measure with R.H.S. chart.
*Pollen*.—Pollen production not observed to date.
Pistil:
*Number*.—2.
*Length*.—Approximately 0.9 cm.
*Style*.—Length: Approximately 0.7 cm. Color: Near R.H.S. Violet-Blue 95C.
*Stigma*.—Shape: rounded. Color: Near R.H.S. Violet-Blue 95C . Ovary Color: Near RHS 145A.

OTHER CHARACTERISTICS

Disease and pest resistance: Not observed to be susceptible nor resistant to normal diseases and pests of *Eryngium zabelii*.
Temperature tolerance: USDA Zone 5 through 9.
Fruit/seed production: Not observed to date.

What is claimed is:

1. A new and distinct cultivar of *Eryngium* plant named 'NEPTUNES GOLD' as herein illustrated and described.

* * * * *